(12) United States Patent
Dahan et al.

(10) Patent No.: US 8,021,046 B2
(45) Date of Patent: Sep. 20, 2011

(54) MEDICAL IMAGING SYSTEM WITH A REMOTE FLUID COOLANT CIRCULATION PUMP RELATIVELY TO ITS X RAY EMITTING TUBE

(75) Inventors: Frédéric Dahan, Le Chesnay (FR); Philippe Blin, Maurepas (FR); Isabelle Berangere Rouzou, Buc (FR); Jean-Marie Penato, Les Essarts le Roi (FR); Gwenael Lemarchand, Limours (FR); Pascal Bonnafour, Bussy-Saint-Georges (FR); Thierry Toledo, Yvelines (FR)

(73) Assignee: General Electric Company, Schenectady, NY (US)

( * ) Notice: Subject to any disclaimer, the term of this patent is extended or adjusted under 35 U.S.C. 154(b) by 258 days.

(21) Appl. No.: 12/399,673

(22) Filed: Mar. 6, 2009

(65) Prior Publication Data
US 2009/0245471 A1    Oct. 1, 2009

(30) Foreign Application Priority Data
Mar. 21, 2008   (FR) ...................................... 08 51877

(51) Int. Cl.
*H01J 35/10* (2006.01)
(52) U.S. Cl. ........................................ 378/200; 378/141

(58) Field of Classification Search .................. 378/130, 378/141, 199, 200
See application file for complete search history.

(56) References Cited

U.S. PATENT DOCUMENTS
6,286,998 B1    9/2001   Dilick

FOREIGN PATENT DOCUMENTS
| DE | 102004002716 | 8/2005 |
|---|---|---|
| GB | 557957 | 12/1943 |
| GB | 2102211 | 12/1983 |
| JP | 2000164390 | 6/2000 |
| JP | 2004311170 | 11/2004 |

*Primary Examiner* — Jurie Yun
(74) *Attorney, Agent, or Firm* — Global Patent Operation; Jonathan E. Thomas

(57) ABSTRACT

A medical imaging system including a support, an X-ray emitting tube, and, facing the latter, a detector, the X-ray emitting tube being intended to accept displacements relatively to at least one portion of the support, the system also including a remote piece of equipment providing circulation of an oil intended to provide cooling and electric insulation of the X-ray emitting tube on the one hand, pipes in which said oil circulates, connecting the remote piece of equipment and the X-ray emitting tube, and a device for dehydrating the oil on the other hand, wherein the dehydration device includes means positioned in the circuit through which the oil flows during normal use of said imaging system and which provide or maintain dehydration of said oil during this use.

10 Claims, 3 Drawing Sheets

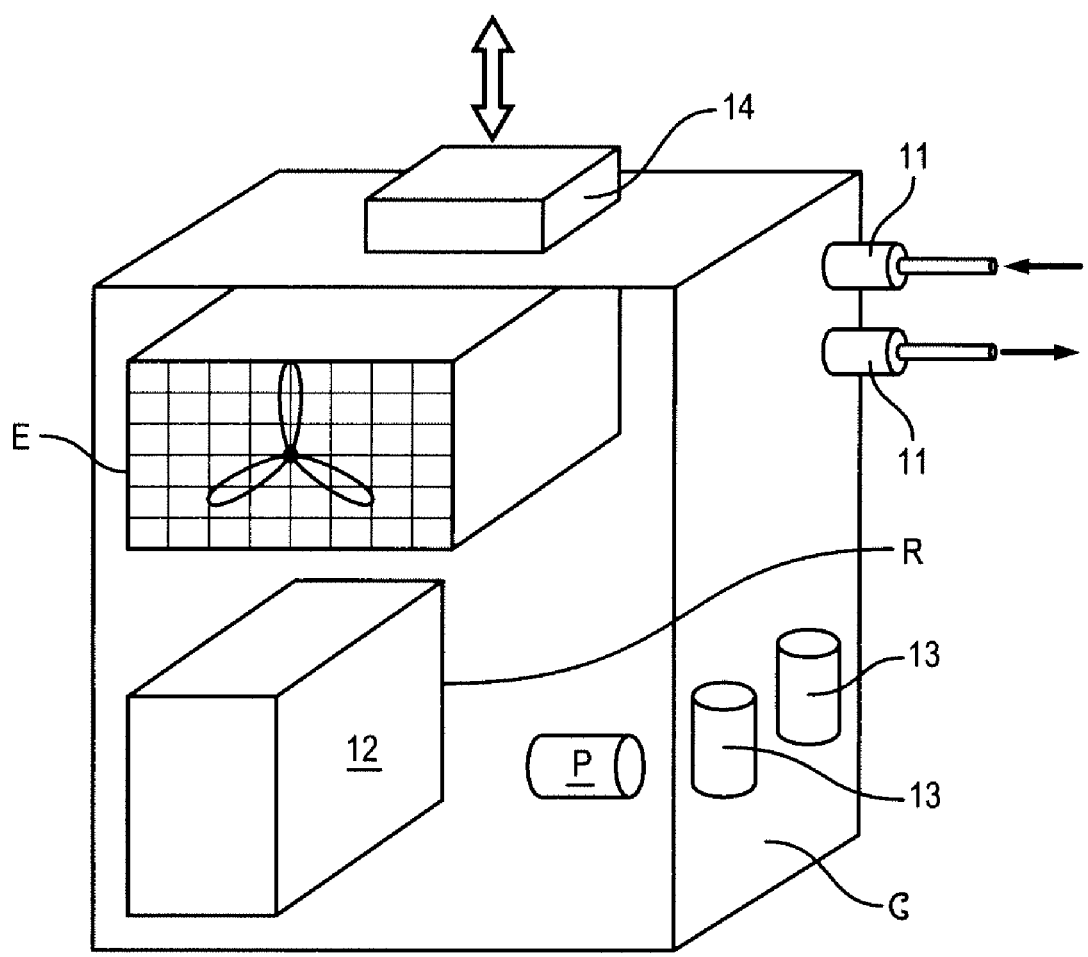
F I G . 3

MEDICAL IMAGING SYSTEM WITH A REMOTE FLUID COOLANT CIRCULATION PUMP RELATIVELY TO ITS X RAY EMITTING TUBE

CROSS-REFERENCE TO RELATED APPLICATIONS

This application claims priority under 35 U.S.C. §119(a)-(d) or (f) to prior-filed, co-pending French patent application serial number 0851877, filed on Mar. 21, 2008, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

The field of the present invention relates to the medical imaging system of the type with an X-ray emitting tube.

2. Description of Related Art

X-ray tubes used in the medical field are of a known conventional structure. They generally include, as illustrated in FIG. 1, an emissive cathode 1 and a rotating anode 2 which forms the target of the electrons emitted by the cathode 1 and which is the location for producing X-rays. This rotating anode 1 is mounted on the rotor of a motor 3. The cathode 1, the anode 2 and the motor 3 are positioned in a metal or glass envelope 4, in which a high vacuum is established.

It will be noted that such X-ray tubes—to which very high voltages (100-150 kV) are applied—have very low yield and are the source of significant heat releases. This is the reason why provision is generally made for having a dielectric coolant oil circulate between the envelope 4 and an external sheath 5. For this purpose, a pump P is usually associated with the X-ray tube. This pump P will cause the oil to circulate between the envelope 4 and the sheath 5, and will send it back into a heat exchanger E for example with plates and cooling by circulation of water or with fins and cooling by air.

Generally, the possibility of strongly lightening the weight of the source of radiation and of reducing the volume is desired so as to allow faster displacements of the latter with more significant offsets if need be.

This is why it has already been proposed to move away the portion of the cooling circuit formed by the pump and the heat exchanger, for example into a maintenance room in the vicinity of the room in which the remainder of the imaging system is set up.

As this will be easily understood, this assumes the setting up of relatively long pipework in order to allow the fluid to circulate between this maintenance room and the X-ray tube. Lengths which may range up to 70 m or more are notably contemplated.

The materials of the pipes contemplated to this day for these applications are relatively permeable to moisture and loaded with water. Other sources of moisture exist, such as the expansion volume, the seal gaskets, the plastic materials, etc.

Now, in order to provide the sought-after electric insulation for the X-ray sources used in the field of medical imaging, the coolant oil should be very slightly loaded with moisture.

Medical imaging systems are already known from U.S. Pat. No. 6,286,998, which include dehydration systems used for dehydrating dielectric oil during the maintenance sequence outside the normal operation of the imaging system.

Such systems remain complex.

Moreover, further improvement of the quality of the dehydration of the dielectric oil is desired in order to attain better performance.

BRIEF SUMMARY OF THE INVENTION

An embodiment of the invention provides a structure for an imaging system which should be simple and allow operation with a remote cooling pump, while allowing moisture levels, required for the dielectric efficiency of the coolant oil which is circulated at the level of the tube.

More specifically, an embodiment of the invention provides a medical imaging system including a support, an X-ray emitting tube and, facing the latter, a detector, the X-ray emitting tube being intended to accept displacements relatively to at least one portion of the support, the system also including a remote piece of equipment providing circulation of an oil intended to provide cooling and electric insulation of the X-ray emitting tube on the one hand, tubes in which said oil circulates, connecting the remote piece of equipment and the X-ray emitting tube, and a device for dehydrating the oil on the other hand, characterized in that the dehydration device includes means positioned in the circuit through which the oil flows during normal use of said imaging system and which provide or maintain dehydration of said oil during this use.

An embodiment of the invention also provides a dehydration method in which dehydration of the oil is implemented in the circuit through which the oil flows during normal use of the imaging system and said dehydration of the oil is provided or maintained during this use.

It will be noted that such a dehydration—in the coolant oil circuit—whether dehydration is continuous or intermittent, for example triggered by moisture thresholds in the oil, provides exceptional oil dehydration rates without any human intervention or addition of maintenance equipment.

BRIEF DESCRIPTION OF THE DRAWINGS

Other characteristics and advantages of embodiments of the invention will further become apparent from the description which follows, which is purely illustrative and non-limiting and should be read with reference to the appended figures wherein:

FIG. 3 schematically illustrates the remote piece of equipment in the maintenance room;

DETAILED DESCRIPTION OF THE INVENTION

Figure 2:
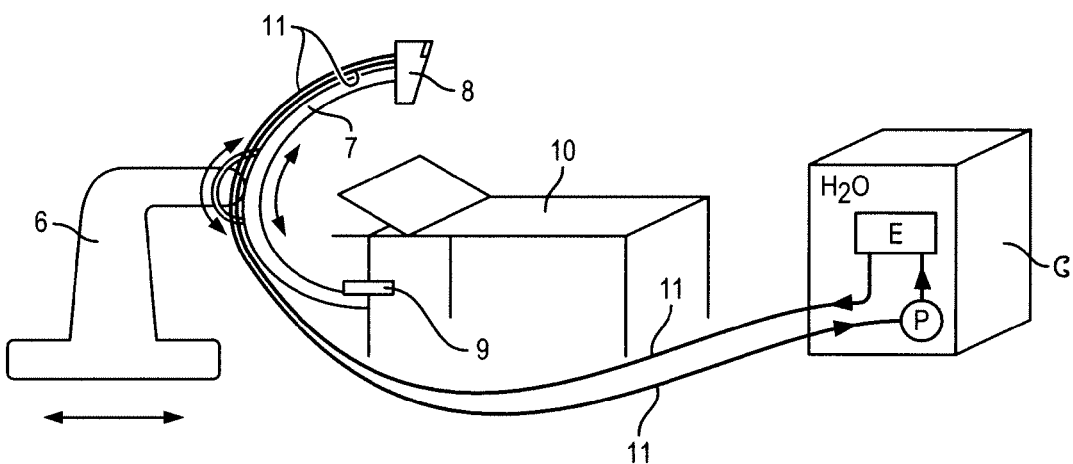
FIG. 2 is a schematic representation illustrating the general structure of an imaging system of the C-arm type with remote pump and cooler relatively to the X-ray tube.

The imaging system illustrated in FIG. 2 in this case is a C-arm type system notably used for interventional vascular imaging applications. It includes a support 6 which bears a C-type arm 7 which itself bears at one of its ends on the one hand an X-ray emitting tube 8 and at its other end a detector 9 on the other hand.

As illustrated by the different double arrows in FIG. 2, the C-arm 7—itself already known—accepts different movements by which it may take images according to various angles around a bed 10 intended to receive the patient. Notably, it may rotate relatively to the support 6 around a horizontal axis; it may swing by translation on itself, the displacement of its support also allows it to perform horizontal displacement movements.

The detector 9 is a matrix detector or a cassette of film sensitive to X-rays for example.

Figure 1:
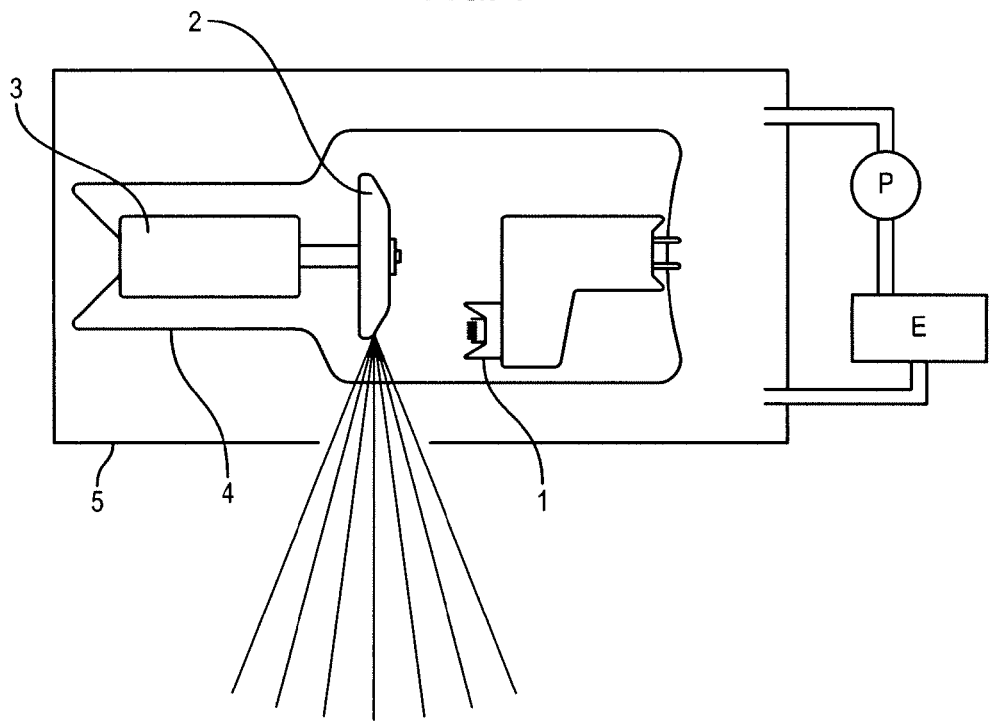
FIG. 1 is a schematic representation illustrating a possible embodiment for an X-ray tube of the type of those used in medical imaging.

As for the tube 8, it has a general structure of the type of the one illustrated in FIG. 1 and described in the preamble of the description, for which the cooling pump P and the heat exchanger E have been moved away, for example into a maintenance room in proximity to the room in which the imaging system is found, in order to reduce the weight borne by the C-arm 7 and the volume occupied by the X-ray source at the latter, but also in order to reduce noise therein.

In FIG. 2, the pump P and exchanger E are positioned in a box C, connected to the X-ray tube through piping 11 passing through the support 6.

This piping 11 for example has some flexibility so that it may accompany the different movements which one wishes to impart to the source around the bed.

These pipes 7 for example are nitrile or polyurethane pipes, with a diameter of the order of 16 to 25 mm. They extend with a length adapted to the configuration of the room in which the system and the additional piece of equipment are set up. This length is for example from 20 to 40 m in the outgoing direction and the same in the incoming direction, the total length may consequently be 70 m or more.

The remote box C is for example set up in a metal casing which, in addition to a water or air heat exchanger E and a pump P, also includes, as illustrated in FIG. 3, an expansion volume 12 for the circulating oil associated with the dehydration means D described in more detail with reference to FIGS. 4A to 4D, as well as filtering means 13. By electronics 14, information on the operation of these different components may be transmitted to a remote control unit and they may be remote-controlled.

The dehydration means D may be in series with the circuit through which the coolant oil flows during operation of the imaging system.

In another embodiment not shown, the dehydration means D may be found in a branch for tapping/injecting oil which is part of the circuit through which the coolant oil flows during operation of the imaging system.

In this embodiment, the oil tapping/injecting branch comprises an upstream fork through which a portion of the oil circulating in the general circuit may be tapped and a downstream fork through which the tapped oil portion may be re-injected into the general circuit. The dehydration means D are positioned on the oil tapping/injecting branch. The tapped oil flow and the dehydration means D are dimensioned so as to guarantee that the dehydrated tapped oil, re-injected and mixed with the oil of the main circuit provides a moisture content of the oil at the tube 8 which complies with the required characteristics.

For reasons of safety (hot portions potentially accessible by personnel) and behaviour over time of the constitutive materials of the sheath of the tube, the temperature of the sheath at the close of an imaging sequence should be limited. Generally, this maximum temperature is of the order of 70° C. The equipment in said box C—and notably with the exchanger E—should allow the oil to be cooled down to a temperature which allows the sheath of the tube to be maintained in the maximum temperature area mentioned above.

In an exemplary embodiment, the temperature of the oil upon entering the box C may be very variable: from room temperature upon starting the machine right up to 80° C. Celsius.

The oil flow rate provided by the pump is for example from 5 to 30 liters per minute, the expansion volume 12 being for example a volume of the order or 10 to 75 liters.

With the dehydration means D and the filtering means 13, it should be possible to maintain the oil dehydrated and particle-filtered to such a degree that it may flow through the pipes in the outcoming direction right up to the X-ray tube while remaining below hydration thresholds and particle load thresholds required for the operation expected for the tube 8, notably in terms of dielectric efficiency of the oil.

As an example, it may be desired that the moisture content of the oil at the tube 8 be permanently less than 20 ppm.

For this purpose the dehydration means D are in the circuit through which the coolant oil flows during operation of the imaging system. They generally use a reservoir R, which coincides with the expansion volume 12 or alternatively differs from the latter. They provide continuous or further intermittent dehydration of the oil, depending on the cycles triggered by the moisture contents as measured on the oil.

Figure 4A:
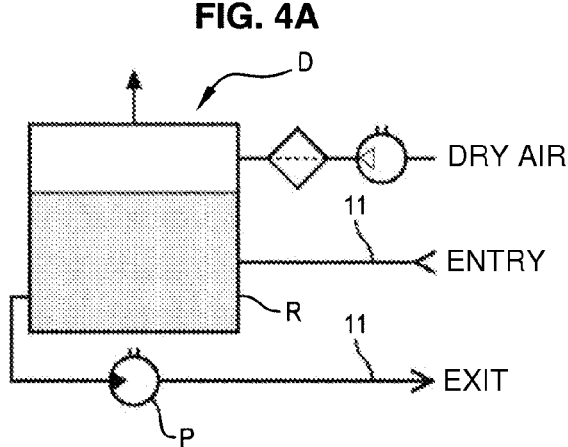
FIGS. 4A, 4B, 4C, 4D, and 4E illustrate several dehydration techniques which may be used for applying embodiments of the invention.

FIG. 4A illustrates a possible embodiment.

In this embodiment, the oil of the reservoir R is in equilibrium with dry air which is circulated continuously or intermittently above this reservoir. As a result, the relative moisture of the oil is set into equilibrium with that of the air of this reservoir. As the air is being permanently dried, the moisture of the oil decreases very rapidly to values corresponding to those sought for dehydration, or even to lower values.

Figure 4B:
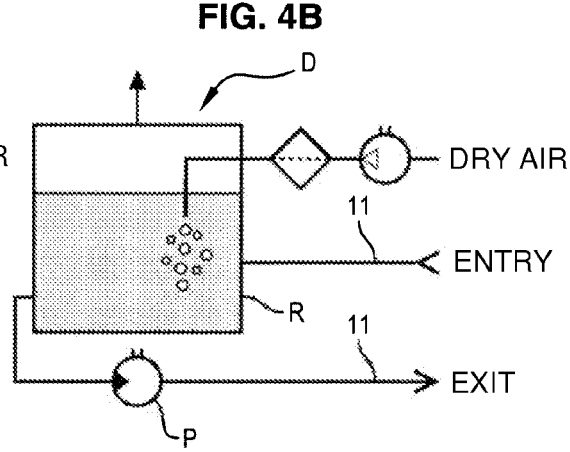

In the embodiment illustrated in FIG. 4B, dry air is injected inside the oil and not above. The drying phenomenon is similar to that of FIG. 4A.

Figure 4C:
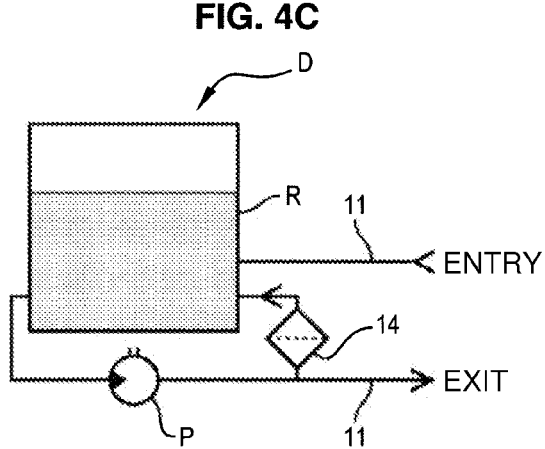

Alternatively, drying the oil may be provided by having it circulate through absorbing/siccative filters 14 mounted in parallel or in series relatively to the main oil circulation circuit (FIG. 4C).

Figure 4D:
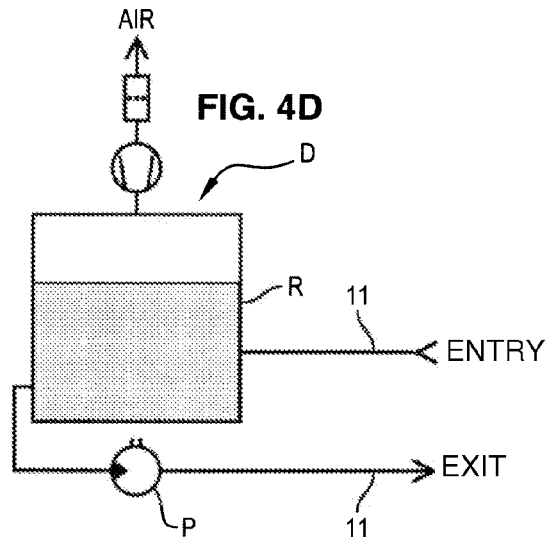

Still alternatively, as illustrated in FIG. 4D, provision may be made for applying vacuum (pump 15) to the reservoir R, so as to dry the oil, by keeping it below the saturation vapour pressure of water.

Figure 4E:
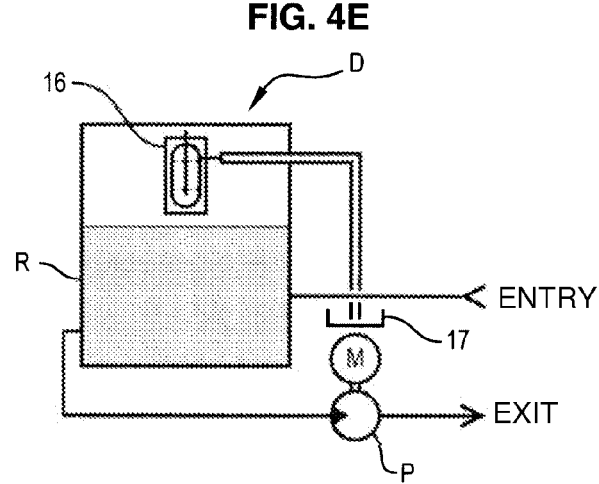

Still alternatively, and as illustrated in FIG. 4E, a Peltier effect cell 16 around which air circulates may be provided inside the expansion chamber above the oil. The moisture contained in the air condenses, and is then sucked up in an evaporator 17, which contributes to drying the air in the reservoir R and so to drying the actual oil.

In FIGS. 4A to 4E, the dehydration reservoir R and the expansion volume 12 coincide; however in embodiments not shown, the dehydration reservoir R and the expansion volume 12 may be independent of each other while communicating with each other.

Further, the dehydration means D may not be in the box C and may be independent of the latter.

Moreover, in another embodiment, the circuit through which the oil flows during normal use of the imaging system may comprise a primary circuit in which a primary oil flow circulates, and a secondary circuit parallel to the primary circuit and in which a secondary oil flow circulates, the dehydration means D being localized on the parallel secondary circuit.

Any other dehydration technique likely to be used during operation of the imaging system may of course be used.

The invention was described herein within the scope of a C-arm imaging system. Of course, it applies to any other type of imaging system with an X-ray emitting tube, and notably for example also to mammography, notably vascular radiography/fluoroscopy apparatuses, or even scanners.

The invention claimed is:

1. A medical imaging system, comprising:
    an X-ray source;
    a heat exchanger; and
    piping fluidly connecting the X-ray source to the heat exchanger,
    wherein the X-ray source, the heat exchanger and the piping define a circuit configured to circulate a coolant between the X-ray source and the heat exchanger; and
    a dehydration device coupled with the circuit to remove moisture from the coolant during normal operation of the X-ray source.

2. The system of claim 1, wherein the dehydration device comprises a coolant reservoir configured to circulate dry air above the coolant.

3. The system of claim 1, wherein the dehydration device comprises a coolant reservoir configured to inject dry air into the coolant.

4. The system of claim 1, wherein the dehydration device comprises:
    a coolant reservoir; and
    a vacuum device configured to apply a vacuum to the reservoir.

5. The system of claim 1, wherein said dehydration device comprises at least one drying/siccative device.

6. The system of claim 1, wherein said dehydration device comprises:
    a coolant reservoir; and
    a Peltier effect cell configured to dry air above the coolant in the reservoir.

7. The system of claim 1, wherein the dehydration device is remote with respect to the X-ray source.

8. A method for dehydrating coolant in a medical imaging system the method comprising:
    flowing coolant through a circuit defined by an X-ray source, a heat exchanger, and piping connecting the X-ray source to the heat exchanger, wherein the circuit is coupled with a dehydration device; and
    dehydrating, using the dehydration device, the coolant during normal operation of the X-ray source.

9. The method according to claim 8, wherein said dehydrating is continuous.

10. The method according to claim 8, wherein said dehydrating is intermittent.

* * * * *